United States Patent
Otsuki et al.

(10) Patent No.: US 7,718,260 B2
(45) Date of Patent: May 18, 2010

(54) HOLLOW FIBER HAVING INNER WALL INTO WHICH COMB POLYMER IS INTRODUCED, HOLLOW FIBER IMPREGNATED WITH GEL, AND THIN SLICE OF FIBER ARRAY

(75) Inventors: Chiuhei Otsuki, Kanagawa (JP); Chiho Itou, Kanagawa (JP); Haruko Miyauchi, Kanagawa (JP); Teruta Ishimaru, Kanagawa (JP); Takashi Akita, Kanagawa (JP); Nobuko Oogami, Osaka (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 541 days.

(21) Appl. No.: 10/484,810

(22) PCT Filed: Jul. 31, 2002

(86) PCT No.: PCT/JP02/07787

§ 371 (c)(1),
(2), (4) Date: Aug. 24, 2004

(87) PCT Pub. No.: WO03/012423

PCT Pub. Date: Feb. 13, 2003

(65) Prior Publication Data

US 2004/0258897 A1   Dec. 23, 2004

(30) Foreign Application Priority Data

Jul. 31, 2001 (JP) ............................... 2001-232751

(51) Int. Cl.
*D01F 6/00* (2006.01)
(52) U.S. Cl. .................. 428/398; 428/396; 428/397

(58) Field of Classification Search ............ 210/500.23, 210/506, 508; 428/396, 398
See application file for complete search history.

(56) References Cited

U.S. PATENT DOCUMENTS

| 3,871,950 | A | * | 3/1975 | Hashino et al. | 428/398 |
| 4,181,694 | A | * | 1/1980 | Hashino et al. | 264/41 |
| 4,780,205 | A | * | 10/1988 | Murakami et al. | 210/321.8 |
| 5,232,642 | A | * | 8/1993 | Kamo et al. | 264/41 |
| 5,998,588 | A | * | 12/1999 | Hoffman et al. | 530/402 |
| 6,001,288 | A | * | 12/1999 | Saruhashi et al. | 264/41 |
| 6,150,459 | A | * | 11/2000 | Mayes et al. | 525/54.1 |
| 6,207,749 | B1 | * | 3/2001 | Mayes et al. | 524/731 |
| 6,399,700 | B2 | * | 6/2002 | Mayes et al. | 524/731 |

(Continued)

FOREIGN PATENT DOCUMENTS

WO    WO 00/53736    *    9/2000

*Primary Examiner*—Jill Gray
(74) *Attorney, Agent, or Firm*—Oblon, Spivak, McClelland, Maier & Neustadt, L.L.P.

(57) ABSTRACT

This invention provides hollow fibers impregnated with gel in which the gel firmly adheres to the inner walls of the hollow fibers due to the introduction of comb polymers on the inner walls of the hollow fibers. These hollow fibers impregnated with gel have no gaps at the interfaces between the inner walls thereof and the gel. Accordingly, analysis can be performed with high accuracy. Also, thin slices obtained by bundling these hollow fibers and then slicing this bundle have sufficient adhesion between the gel and the inner walls of the hollow fibers. This also prevents gel from becoming detached from the inner walls at the time of slicing or during operations such as hybridization.

22 Claims, 1 Drawing Sheet

U.S. PATENT DOCUMENTS

2001/0027237 A1* 10/2001 Mayes et al. ............. 525/326.1
2003/0087111 A1* 5/2003 Hubbell et al. ............. 428/457
2004/0258897 A1* 12/2004 Otsuki et al. ............. 428/292.1
2005/0011826 A1* 1/2005 Childs et al. ............. 210/490

* cited by examiner

HOLLOW FIBER HAVING INNER WALL INTO WHICH COMB POLYMER IS INTRODUCED, HOLLOW FIBER IMPREGNATED WITH GEL, AND THIN SLICE OF FIBER ARRAY

TECHNICAL FIELD

The present invention relates to hollow fibers that are used in capillary electrophoresis or the like or thin slices of a hollow fiber array that are used as, for example, members for DNA microarrays.

BACKGROUND ART

Recently, capillary gel electrophoresis has been employed in order to analyze trace amounts of substances in organisms. The capillaries employed in such a method utilize narrow tubes having inner diameters of about 100 μm. Thus, trace amounts of samples are sufficient for use, and samples can be easily isolated. Members that are used for the capillaries include plastics that are excellent in their transparency, such as those represented by glass or polymethyl methacrylate. Use of capillaries having a hollow portion impregnated with a gel such as acrylamide as a member for a DNA chip that can collectively analyze genes has been attempted (WO 00/53736).

In order to analyze organism-associated substances such as DNA by capillary gel electrophoresis or using DNA chips, gel must be firmly retained inside a capillary.

When the volume of gel filling the hollow portion is reduced, however, a gap is generated at the interface between the inner wall of a capillary and the gel. At the time of analysis, a substance first flows into the generated gap, and this disadvantageously leads to lowered accuracy in analysis. When a capillary is used as a member for a DNA chip, the DNA chip is constructed by, for example, bundling several capillaries and cross-sectioning the bundle. When gel does not sufficiently adhere to the inner wall of the capillary, it disadvantageously becomes detached from the capillary at the time of cross-sectioning. Further, gel becomes detached from the capillary during analysis such as hybridization.

Introduction of a hydrophilic group on the inner wall of the capillary has been proposed as an example of a technique for enhancing adhesion between the inner wall of the capillary and a gel (U.S. Pat. No. 5,015,350). This is, however, a technique for enhancing the adhesion between a gel and the capillary by coating the capillary for hydrophilization. Thus, the strength of the adhesion between a gel and the inner wall is not sufficient, so that gel cannot be retained as the number of times that the capillary is used increases.

In the case of a glass capillary, a method for enhancing the ability of a gel to adhere thereto by chemically modifying the inner wall thereof with polyacrylamide has been developed (S. F. Y. Li et al., Capillary Electrophoresis, 173, 1992). This is, however, a technique for processing a glass surface with a bifunctional coupling agent that reacts with a silanol group on the glass surface. Accordingly, the effect of this technique cannot be attained by non-glass capillaries.

There has been a proposed method in which the shaping of a polymer capillary is conducted simultaneously with gel impregnation of the hollow portion of the capillary, thereby obtaining a polymer capillary having its hollow portion impregnated with a gel (JP Patent Publication (Kokai) No. 11-211694 A (1999)). With this technique, however, a gap is generated at the interface between the inner wall of the capillary and a gel when the volume of the gel is reduced during the shaping of the capillary.

Meanwhile, an attempt has been made in which hollow portions of porous hollow fibers are filled with water-insoluble polymers for the purpose of imparting functions such as hygroscopic properties and antistatic properties (JP Patent Publication (Kokai) No. 8-188967 A (1996)). This is, however, a technique for imparting new functions to fibers, which is unrelated to the adhesiveness of the gel filling the hollow portion.

More specifically, no conventional means had existed in the past that would sufficiently overcome the problem of the gap generated at the interface between the inner wall of the capillary and the gel when the volume of the gel is reduced or the problem of the gel becoming detached from the capillary when a DNA chip is constructed. Thus, it has been difficult to utilize a capillary impregnated with a gel for capillary gel electrophoresis or as a member for a DNA chip.

DISCLOSURE OF THE INVENTION

An object of the present invention is to provide hollow fibers that can firmly retain gel on the inner walls of their hollow portions. It is another object of the present invention to provide hollow fibers having their hollow portions impregnated with gel. It is a further object of the present invention to provide thin slices obtained by slicing a bundle of hollow fibers having firmly immobilized gel in their hollow portions.

The present inventors have conducted concentrated studies in order to attain the above objects. As a result, they have found that introduction of comb polymers on the inner walls of hollow fibers resulted in enhanced adhesion between the inner walls of hollow fibers and the gel filling the hollow portions. This can prevent, for example, the gel from becoming detached from the inner walls of hollow fibers when the volume of the gel is reduced, or when the DNA chip is constructed. This has led to the completion of the present invention.

More specifically, the present invention is as described below.

1. Hollow fibers having comb polymers introduced on their inner walls.

Examples of comb polymers include those having polymerizable functional groups or hydrophilic functional groups. An example of the backbone of the comb polymer is polymethyl methacrylate.

2. Hollow fibers having their hollow portions impregnated with gel.

An example of a gel is one mainly composed of an acrylamide monomer. Such gel retains an organism-associated substance according to need.

3. A hollow fiber array prepared by bundling several hollow fibers impregnated with gel.

4. Thin slices of the hollow fiber array prepared by cross-sectioning the array according to 3.

The hollow fibers used in the present invention are organic fibers. Examples thereof include: polyamide fibers such as Nylon 6, Nylon 66, and aromatic polyamide fibers; polyester fibers such as polyethylene terephthalate, polybutylene terephthalate, polylactic acid, polyglycolic acid, and polycarbonate fibers; acrylic fibers such as polyacrylonitrile fibers; polyolefin fibers such as polyethylene and polypropylene fibers; polymethacrylate fibers such as polymethylmethacrylate fibers; polyvinyl alcohol fibers; polyvinylidene chloride fibers; polyvinyl chloride fibers; polyurethane fibers; phenolic fibers; fluorine fibers comprising polyvinylidene fluoride or polytetrafluoroethylene; and polyalkylene paraoxybenzoate fibers.

Analysis by capillary electrophoresis is conducted by radiating light for detection from the outer wall side of the capillary. Thus, hollow fibers are preferably optically transparent, and examples of preferable materials for hollow fibers are methacrylic resins exemplified by polymethyl methacrylate (PMMA), polystyrene, or polycarbonate that have excellent transparency.

Hollow fibers may be porous or non-porous. The outer diameters of hollow fibers are 2 mm or smaller, and preferably 1 mm or smaller. The inner diameters thereof are preferably 0.02 mm or larger.

In the present invention, the comb polymers that are introduced on the inner walls of the hollow fibers are composed of backbones (main chains) and side chains (branches), and examples thereof are shown in (a) or (b) below. These comb polymers allow the gel filling the hollow portions to be firmly retained on the inner walls of hollow fibers.

(a) Comb Polymers Having Polymerizable Functional Groups on their Main or Side Chains Examples of polymerizable functional groups include vinyl, acrylate, methacrylate, and cyclic unsaturated functional groups such as cyclohexene groups. These polymerizable functional groups are preferably introduced at terminuses of main or side chains of comb polymers.

Polymer components that are used as main chains of comb polymers preferably have affinity to a material used for hollow fibers. When a material used for hollow fibers is polymethyl methacrylate (PMMA), monomer components that are used as main chains of comb polymers are preferably, for example, methyl methacrylate, methyl acrylate, 2-hydroxyethyl methacrylate, acrylic acid, methacrylic acid, glycidyl methacrylate, 2,3-dihydroxypropyl methacrylate, glycerol methacrylate, 2-hydroxyethyl acrylate, or 2-hydroxypropyl acrylate. Two or more kinds of these monomers can be copolymerized.

(b) Comb Polymers Having Affinity to a Gel Filling the Hollow Portions

As with the case of (a) above, polymer components that are hydrophilic with materials used for hollow fibers should be selected as polymer components for main chains. Preferably, polymer components of side chains have affinity sufficiently to the network structure of the gel filling the hollow portion of the hollow fibers and are capable of becoming entangled with the network structure of a polymeric gel.

For example, if the gel filling the hollow portion is hydrophilic, a side chain polymer preferably has a hydrophilic functional group. Examples of a hydrophilic functional group include a polymer comprising hydroxyethyl methacrylate, ethylene glycol, propylene glycol, vinyl alcohol, acrylic acid, or acrylamide as a constitutional unit or a copolymer of two or more thereof. In addition thereto, a polymer comprising a hydrophilic functional group such as a hydroxyl, amino, or sulfonic acid group introduced at its terminus can be selected as a side chain.

The molecular weight of the polymer that is introduced on the side chain is preferably between 20 and 300,000, and more preferably between 1,000 and 10,000.

Comb polymers can be introduced on the inner wall of the hollow fiber by immersing one end of the hollow fiber in a solution of comb polymers and suctioning the solution from the other end. In such a case, the solution of comb polymers introduced by suction is preferably discharged in order to avoid blockage in the hollow portion or embrittlement of hollow fibers caused by dissolution of inner walls of hollow fibers. After the polymer solution is discharged, a solvent that dissolves the comb polymers is allowed to evaporate by air-drying, and the comb polymers are then allowed to adhere to the inner walls of hollow fibers.

The concentration of the comb polymers are preferably 50% by mass or lower, and more preferably 1% to 10% by mass.

In order to allow the comb polymers described in (a) and (b) above to uniformly adhere to the inner walls of hollow fibers, a solvent that dissolves the comb polymers is preferably a good solvent for the comb polymers and a poor solvent for materials used for hollow fibers. Examples of preferable solvents include alcohols such as methanol, ethanol, and propanol, acetone, methyl ethyl ketone, acetonitrile, dioxane, dimethylformamide, dimethylacetamide, dimethylsulfoxide, toluene, and ethyl acetate. These solvents can be used solely or in combinations of two or more. When several solvents are used in combination, the solvents to be combined are preferably miscible with each other, and solvents to be mixed are preferably solely good solvents for the comb polymers.

In the present invention, the kinds of gel used to fill the hollow portions are not particularly limited. Examples of a gel that can be used include a gel prepared by allowing a cross-linked polymer to swell with the aid of water, wherein the cross-linked polymer is prepared by copolymerizing at least one monomer selected from among acrylamide, N,N-dimethylacrylamide, N-isopropylacrylamide, N-acryloylaminoethoxyethanol, N-acryloylaminopropanol, N-methylolacrylamide, N-vinylpyrrolidone, hydroxyethyl methacrylate, (meth)acrylic acid, allyl dextran, and the like with a polyfunctional monomer such as methylene bis(meth)acrylamide, or polyethylene glycol di(meth)acrylate.

Examples of polymerization initiators that can be used include azo, peroxide, or redox initiators that can be dissolved in the solvent to be used. Examples thereof include 2,2'-azobisisobutyronitrile, 2,2'-azobis(2-methyl butyronitrile) isobutyronitrile, benzoyl peroxide, and benzoyl peroxide/dimethylaniline.

Examples of other gels include gels such as agarose, alginic acid, dextran, polyvinyl alcohol, or polyethylene glycol and gels prepared by cross-linking these gels.

When the hollow fibers of the present invention are used for nucleic acid analysis, the gel used to fill the hollow portion is preferably an acrylamide gel. The concentration level of an acrylamide monomer is preferably 2% to 20% by mass.

A gel is commonly used to fill the hollow portion of the hollow fiber through suction in vacuo, although the technique used therefor is not limited thereto.

When the comb polymer as described in (a) above is used, a polymerizable functional group thereof is chemically bound to a gel component, thereby allowing the gel used to fill the hollow fibers to be firmly retained on the inner walls of the hollow fibers. More specifically, a monomer component, which is a starting material for a gel component, fills the hollow fiber comprising the comb polymer described in (a) introduced on its inner wall, and a polymerizable functional group of the comb polymer described in (a) is allowed to react with the monomer component when polymerizing monomer components.

When the comb polymer described in (b) above is used, a gel filling the hollow fiber can be firmly retained on its inner wall upon the entanglement of the network structure of the gel filling the hollow fiber and the side chain of the comb polymer (b).

In the present invention, examples of organism-associated substances include those selected from the group consisting of the following substances 1 to 3:

1. a nucleic acid, amino acid, sugar, or lipid;
2. a polymer comprising at least one of substance 1. above; and
3. a substance interacting with substance 1 or 2.

When a nucleic acid is used as an organism-associated substance, for example, DNA can be prepared from a living cell by the method of Blin et al. (Nucleic Acids Res. 3. 2303, 1976), and RNA can be extracted therefrom by the method of Favaloro et al. (Methods. Enzymol. 65, 718, 1980). Also, chain or cyclic plasmid DNA or chromosome DNA can be used. A DNA fragment that has been cleaved with a restriction enzyme or chemically, DNA that has been synthesized with the aid of an enzyme or the like in vitro, or DNA that has been synthesized chemically can be used as such DNA.

Organism-associated substances can be retained by the gel by physically embedding them in the gel or directly binding them to gel constituents. Alternatively, organism-associated substances may be first allowed to bind to carriers such as polymers or inorganic particles by covalent or non-covalent bonds, thereby immobilizing the carriers in the gel.

An embodiment of a direct bond to a gel constituent is carried out by introducing a vinyl group to a nucleic acid terminus and then allowing the resultant to copolymerize with a gel constituent, such as acrylamide (WO 98/39351). Also, agarose is converted to imide carbonate by the cyanogen bromide method, and the resultant is bound to an amino group of a nucleic acid having an aminated terminus, thereby gelating the agarose. Alternatively, a biotinized nucleic acid can be allowed to react with avidinized agarose beads (for example, avidinized agarose, manufactured by Sigma), thereby obtaining agarose beads having nucleic acids immobilized thereon. The agarose beads having nucleic acids immobilized thereon can be immobilized in acrylamide gel or the like.

Several hollow fibers comprising the thus prepared gel comprising an organism-associated substance retained thereby filling their hollow portions are bundled, and the bundle of fibers is cross-sectioned. Thus, thin slices of the hollow fiber array can be prepared.

Examples of methods for bundling several hollow fibers include: (a) a method in which several hollow fibers are arranged in parallel and immobilized on a sheet such as an adhesive sheet, and the sheet is wound in a spiral configuration, thereby forming a bundle; and (b) a method in which two porous plates with several openings are stacked, a hollow fiber is allowed to pass through each opening of these porous plates, and the interval between two porous plates is widened, thereby forming a bundle.

In the method as described in (b) above, a tension should be imparted to each fiber in order to maintain the regularity of the sequence after the fibers have been allowed to pass through the porous plates. Accordingly, fibers are preferably highly elastic, and examples thereof include materials comprising methacrylic resins such as aromatic polyamide or methyl methacrylate.

A bundle of hollow fibers is immobilized by causing resins or the like to flow into the gap between two fibers. The immobilized bundle of fibers is cross-sectioned using a microtome or the like. Thus, thin slices can be obtained. The thin slices preferably have thicknesses of 1 mm or smaller.

The thin slices are employed for the collective analysis of several genes. Thus, the number of hollow fibers in one thin slice is preferably large. Preferably, 100 or more fibers are present per $cm^2$ thereon. The outer diameters of the hollow fibers used are preferably small. They are preferably 0.5 mm or smaller, and further preferably 0.3 mm or smaller. The inner diameters are preferably 0.02 mm or larger.

Organism-associated substances that are retained in hollow fibers in thin slices may differ depending on the type of hollow fiber. Alternatively, a group of several hollow fibers comprising the same organism-associated substances being retained therein may be placed in thin slices.

The thus prepared thin slices of hollow fiber arrays retaining organism-associated substances are used as, for example, a tool for collective analysis of genes.

This description includes part or all of the contents as disclosed in the description of Japanese Patent Application No. 2001-232751, which is a priority document of the present application.

BEST MODES FOR CARRYING OUT THE INVENTION

Figure 1:
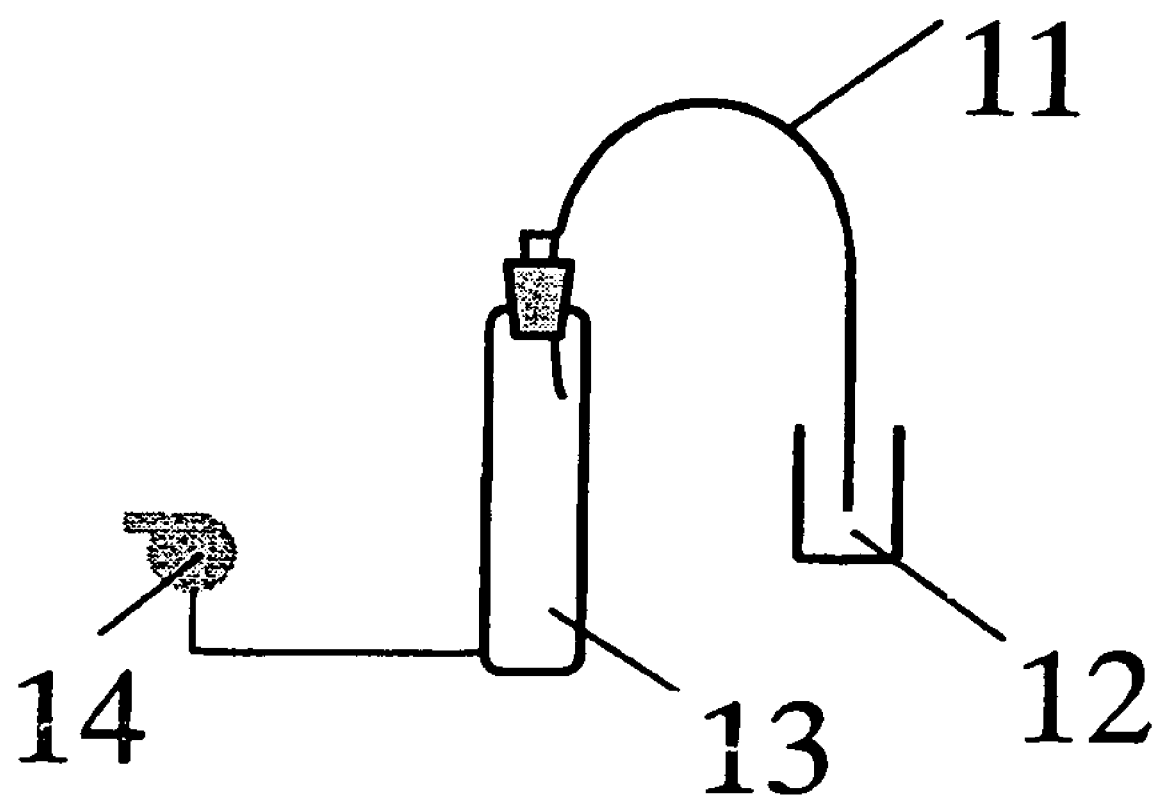
FIG. 1 schematically shows an apparatus for introducing a solution of comb polymers on the inner walls of hollow fibers, wherein reference numeral 11 indicates a bundle of fibers, reference numeral 12 indicates a vessel filled with a solution of comb polymers, reference numeral 13 indicates a trap tube, and reference numeral 14 indicates a vacuum pump.

The present invention is described in greater detail with reference to the following examples.

Example 1

(1) Production of Comb Polymers Having Polymerizable Functional Groups on their Side Chains Methyl methacrylate (MMA, 100 parts), glycidyl methacrylate (GMA, 100 parts), and azobisisobutyronitrile (AIBN, 0.5 parts) were added dropwise to methyl ethyl ketone (MEK, 50 parts) at 80° C. in the nitrogen gas stream (50 cc/min) for 3 hours.

Thereafter, AIBN (0.1 parts) and MEK (70 parts) were added, the resultant was allowed to stand for 1 hour, AIBN (0.1 parts) and MEK (10 parts) were added, the resultant was allowed to stand for 3 hours, and MEK (50 parts) was further added. Thereafter, methylhydroquinone (MEHQ, 0.5 parts), triphenylphosphine (2.5 parts), and acrylic acid (99 mole % of GMA) were added. During these procedures, reaction was allowed to proceed for 30 hours while air was blown thereinto (100 cc/min), and comb polymers (A) having vinyl groups added to their side chain terminuses were obtained. These copolymers had 25 mole % of vinyl groups introduced therein.

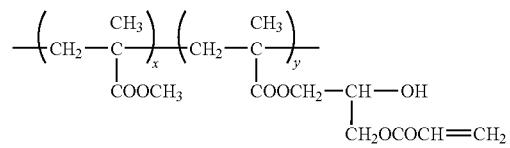

(2) Production of Hollow Fibers Comprising Comb Polymers Introduced Therein 50 hollow fibers of polymethyl methacrylate (outer diameter: 300 μm, inner diameter: 200 μm, length: 60 cm, manufactured by Mitsubishi Rayon Co., Ltd.) were bundled, and comb polymers (A) were introduced in their hollow portions using the apparatus shown in FIG. 1. In FIG. 1, one end of fiber bundle 11 was connected to trap tube 13. Another end was placed in vessel 12 filled with polymer solution 1. Vacuum pump 14 was activated to introduce the polymer solution 1 in the hollow portions by suction.

A part of the solution introduced by suction into the hollow portions was transferred to the trap tube, and the solvent remaining on the inner walls of the hollow portions was allowed evaporate by air drying. Thus, hollow fibers, the comb polymers (A) having been introduced on the inner walls of their hollow portions, were obtained.

| [Polymer solution 1] | |
|---|---|
| Comb polymer (A) | 5% by mass |
| 1,4-dioxane | 95% by mass |

(3) Production of a Hollow Fiber Array

Two porous plates (thickness: 0.1 mm) each comprising 49 pores in total arranged in 7 rows in both lengthwise and breadthwise directions, having pore diameters of 0.32 mm, and having the center-to-center distances between neighboring pores of 0.42 mm were stacked. 49 hollow fibers of polymethyl methacrylate prepared in (2) above were allowed to pass through each pore of these two porous plates. The interval between the two porous plates was 50 mm, and both ends were immobilized while threads were being stretched therebetween.

Subsequently, a starting material for resin was made to flow into the vicinity of the hollow fiber array and then allowed to harden. Polyurethane resin adhesives (Nippolan 4276, Coronate 4403, manufactured by Nihon Polyurethane Industry Co., Ltd.) were used. After the resin had hardened, the porous plates were removed. Thus, a resin block containing hollow fibers was obtained.

(4) Production of Oligonucleotide Having a Methacrylate Group

An oligonucleotide was synthesized using an automatic DNA/RNA synthesizer (model 1394, manufactured by Applied BioSystems (formerly PE Biosystems)). In the final step of synthesis, the reaction was allowed to proceed using Aminolink II (manufactured by Applied BioSystems) to synthesize an oligonucleotide having aminated terminuses.

The resulting GCAT with aminated terminuses (50 µl, 500 nmol/ml), glycidyl methacrylate (5 µl), and dimethylformamide (DMF, 5 µl) were mixed, the mixture was allowed to react at 70° C. for 2 hours, and 190 µl of water was added thereto. Thus, GCAT having 100 nmol/ml of methacrylate groups (MA-GCAT) was obtained.

(5) Impregnation of Hollow Portions with Gel

Subsequently, a starting solution for a gel comprising the monomer and the initiator with the following mass ratios was prepared.

| | |
|---|---|
| Acrylamide | 9 parts by mass |
| N,N-methylenebisacrylamide | 1 part by mass |

| -continued | |
|---|---|
| 2,2'-azobis(2-methylpropionamidine) dihydrochioride (V-50) | 0.1 part by mass |
| Water | 90 parts by mass |

MA-GCAT prepared in (4) was added to the above solution in such a manner that the solution would comprise MA-GCAT at 0.5 nmol/l.

The hollow portions of hollow fibers in the resin block obtained in (3) were filled with this mixed solution, the block was transferred into a hermetically sealed glass vessel with its inside being saturated with moisture, and the content of the vessel was allowed to stand at 70° C. for 3 hours for polymerization. Thus, a gel was generated, and a block of a hollow fiber array having its hollow portion impregnated with gel was obtained.

(6) Production of Thin Slices of a Hollow Fiber Array

This block of hollow fiber array was sliced to a thickness of 500 µm in a direction vertical to the direction of fibers to obtain thin slices. Gel did not become detached from the inner walls at the time of slicing. Thus, it was confirmed that the adhesion at the interface between the inner walls of the hollow fibers and the gel was sufficiently strong. The conditions of the gel in the hollow portions were observed using a stereoscopic microscope. As a result, all the 49 hollow fibers were impregnated with acrylamide gel without any spaces.

Example 2

Thin slices of a hollow fiber array were prepared in the same manner as in Example 1, except that polymer solution 2 was used instead of polymer solution 1.

| [Polymer solution 2] | |
|---|---|
| PMMA monoacrylate (molecular weight: 6,000) | 5 parts by mass |
| Toluene | 95 parts by mass |

Gel did not become detached from the inner walls at the time of slicing. Thus, it was confirmed that the adhesion at the interface between the inner walls of the hollow fibers and the gel was sufficiently strong. The conditions of the gel in the hollow portions were observed using a stereoscopic microscope. As a result, all the 49 hollow fibers were impregnated with acrylamide gel without any spaces.

Example 3

Thin slices of a hollow fiber array were prepared in the same manner as in Example 1, except that hollow fibers of polycarbonate (outer diameter: 250 µm, inner diameter: 130 µm, length: 60 cm, Mitsubishi Rayon Co., Ltd.) were used instead of hollow fibers of polymethyl methacrylate, and polymer solution 3 was used instead of polymer solution 1.

| [Polymer solution 3] | |
|---|---|
| Comb polymer (A) | 5 parts by mass |
| 1,4-dioxane/acetonitrile (12%/88%) | 95 parts by mass |

Gel did not become detached from the inner walls at the time of slicing. Thus, it was confirmed that the adhesion at the interface between the inner walls of the hollow fibers and the gel was sufficiently strong. The conditions of the gel in the hollow portions were observed using a stereoscopic microscope. As a result, all the 49 hollow fibers were impregnated with acrylamide gel without any spaces.

Example 4

(1) Production of Comb Polymers Having Affinity to a Gel Filling Hollow Portions-1

The comb polymer (A) obtained in Example 1 (1 part) and 2,2'-azobis(2-methylpropionamidine) dihydrochloride (V-50, 0.1 parts) as an initiator were placed in a polymerization tube, they were dissolved in 100 parts of hydroxyethyl methacrylate (HEMA), the inside of the tube was deaerated, and the tube was then sealed to conduct polymerization at 60° C. After the completion of the polymerization, the sealed tube was opened and the content thereof was poured into ethanol. Thus, a precipitate of the comb polymer (B) having poly-HEMA added to its side chain was obtained. A homopolymer of HEMA as a by-product was supplemented in an ethanol phase.

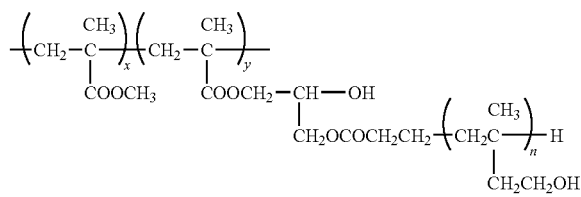

(2) From Introduction of Comb Polymers to Production of Thin Slices of Hollow Fiber Array Thin slices of a hollow fiber array were prepared in the same manner as in Example 1, except that polymer solution 4 was used instead of polymer solution 1.

| [Polymer solution 4] | |
|---|---|
| Comb polymer (B) | 5 parts by mass |
| 1,4-dioxane | 95 parts by mass |

Gel did not become detached from the inner walls at the time of slicing. Thus, it was confirmed that the adhesion at the interface between the inner walls of the hollow fibers and the gel was sufficiently strong. The conditions of the gel in the hollow portions were observed using a stereoscopic microscope. As a result, all the 49 hollow fibers were impregnated with acrylamide gel without any spaces.

Example 5

Thin slices of a hollow fiber array were prepared in the same manner as in Example 3, except that polymer solution 5 was used instead of polymer solution 3.

| [Polymer solution 5] | |
|---|---|
| Comb polymer (B) | 5 parts by mass |
| 1,4-dioxane/acetonitrile (12%/88%) | 95 parts by mass |

Gel did not become detached from the inner walls at the time of slicing. Thus, it was confirmed that the adhesion at the interface between the inner walls of the hollow fibers and the gel was sufficiently strong. The conditions of the gel in the hollow portions were observed using a stereoscopic microscope. As a result, all the 49 hollow fibers were impregnated with acrylamide gel without any spaces.

Example 6

(1) Production of Comb Polymers Having Affinity to a Gel Filling Hollow Portions-2

The comb polymer (A) obtained in Example 1 (1 part) and V-50 (0.1 parts) as an initiator were placed in a polymerization tube, they were dissolved in 100 parts of polyethylene glycol monoacrylate (manufactured by Aldrich), and the tube was then sealed to conduct polymerization at 60° C. After the completion of the polymerization, the solution was poured into water. Thus, the comb polymer (C) having polyethylene glycol added to its side chain was obtained. A homopolymer of polyethylene glycol monoacrylate as a by-product was separated in an aqueous phase.

(2) From Introduction of Comb Polymers to Production of Thin Slices of Hollow Fiber Array Thin slices of a hollow fiber array were prepared in the same manner as in Example 1, except that polymer solution 6 was used instead of polymer solution 1.

| [Polymer solution 6] | |
|---|---|
| Comb polymer (C) | 5 parts by mass |
| 1,4-dioxane | 95 parts by mass |

Gel did not become detached from the inner walls at the time of slicing. Thus, it was confirmed that the adhesion at the interface between the inner walls of the hollow fibers and the gel was sufficiently strong. The conditions of the gel in the hollow portions were observed using a stereoscopic microscope. As a result, all the 49 hollow fibers were impregnated with acrylamide gel without any spaces.

Example 7

(1) Production of Comb Polymers Having Affinity to a Gel Filling Hollow Portions-3

The comb polymer (A) obtained in Example 1 (1 part) and acrylamide (100 parts) were dissolved in 100 parts of ethanol, and an initiator solution (an aqueous solution of 10% ammonium persulfate, 0.1 parts) was added thereto to conduct polymerization at 60° C. After the completion of the polymerization, the solution was poured into water. Thus, the comb polymer (D) having polyacrylamide added to its side chain was obtained. Polyacrylamide as a by-product was separated in an aqueous phase.

(2) From Introduction of Comb Polymers to Production of Thin Slices of Hollow Fiber Array Thin slices of a hollow fiber array were prepared in the same manner as in Example 1, except that polymer solution 7 was used instead of polymer solution 1.

| [Polymer solution 7] | |
|---|---|
| Comb polymer (D) | 5 parts by mass |
| 1,4-dioxane | 95 parts by mass |

Gel did not become detached from the inner walls at the time of slicing. Thus, it was confirmed that the adhesion at the interface between the inner walls of the hollow fibers and the gel was sufficiently strong. The conditions of the gel in the hollow portions were observed using a stereoscopic microscope. As a result, all the 49 hollow fibers were impregnated with acrylamide gel without any spaces.

Comparative Example 1

Thin slices of a hollow fiber array were prepared in the same manner as in Example 1, except that polymer solution 8 was used instead of polymer solution 1.

| [Polymer solution 8] | |
|---|---|
| Copolymer of methyl methacrylate and methacrylic acid (Coating Resin PB 2322, manufactured by Mitsubishi Rayon Co., Ltd.) | 5 parts by mass |
| Ethanol | 95 parts by mass |

The conditions of the gel in the hollow portion were observed. As a result, it was found that none of the gel had become detached from the hollow portion, although a gap was observed at the interface between the inner wall of the hollow fiber and the gel.

All publications, patents, and patent applications cited herein are incorporated herein by reference in their entirety.

INDUSTRIAL APPLICABILITY

Use of hollow fibers having comb polymers introduced on their inner walls can provide hollow fibers impregnated with gel in which the gel is firmly retained on the inner walls of hollow fibers. Thin slices obtained by bundling these hollow fibers and slicing the bundle have sufficient adhesion between the gel and the inner walls of hollow fibers.

The invention claimed is:

1. Hollow fibers impregnated with gel and having comb polymers introduced on their inner walls, wherein the hollow portions of the hollow fibers are filled with gel, and wherein the hollow fibers are non-porous.

2. The hollow fibers impregnated with gel according to claim 1, wherein the gel is mainly composed of an acrylamide monomer.

3. Hollow fibers impregnated with gel, wherein organism-associated substances are retained in the gel in the hollow fibers impregnated with gel according to claim 1.

4. A hollow fiber array, wherein several of the hollow fibers impregnated with gel according to claim 1 are bundled.

5. The hollow fiber array according to claim 4, which comprises 100 or more fibers per $cm^2$ thereon.

6. Thin slices of the hollow fiber array, which are prepared by cross-sectioning the hollow fiber array according to claim 4.

7. The hollow fiber array of claim 4, wherein the fibers are bundled lengthwise and the hollow fiber array has at least one face defined by a single plane comprising a plurality of pores, each pore corresponding with a face of one of the hollow fibers.

8. The hollow fibers according to claim 1, wherein the gel is immobilized on the inner walls of the hollow fibers.

9. The hollow fibers of claim 1, wherein the comb polymers have polymerizable functional groups.

10. The hollow fibers of claim 1, wherein the comb polymers have hydrophilic functional groups.

11. The hollow fibers of claim 10, wherein the comb polymers have at their side chain a polymer selected from the group consisting of polyhydroxyethylmethacrylate, polyethyleneglycol, polyacrylamide, and mixtures thereof.

12. A hollow fiber impregnated with gel and having one or more comb polymers introduced on an inner wall, wherein the hollow portion of the hollow fiber is filled with gel, and wherein the hollow fiber is a non-porous capillary.

13. The hollow fiber of claim 12, wherein the gel mainly comprises an acrylamide monomer.

14. The hollow fiber of claim 12, wherein one or more organism-associated substances is retained in the gel in the hollow fibers.

15. A hollow fiber array, comprising: a plurality of the hollow fibers of claim 12, wherein the fibers are bundled.

16. The hollow fiber array of claim 15, which comprises 100 or more of the fibers per $cm^2$.

17. A thin slice of a hollow fiber array, prepared by cross-sectioning the hollow fiber array of claim 16.

18. The hollow fiber array of claim 15, wherein the fibers are bundled lengthwise and the hollow fiber array has at least one face defined by a single plane comprising a plurality of pores, each pore corresponding with a face of one of the hollow fibers.

19. The hollow fiber of claim 12, wherein the gel is immobilized on the inner wall of the hollow fiber.

20. The hollow fiber of claim 12, wherein the comb polymer has one or more polymerizable functional groups.

21. The hollow fiber of claim 12, wherein the comb polymer has one or more hydrophilic functional groups.

22. The hollow fiber of claim 21, wherein the comb polymer has as a side chain at least one polymer selected from the group consisting of polyhydroxyethylmethacrylate, polyethyleneglycol and polyacrylamide.

* * * * *